(12) United States Patent
Lee et al.

(10) Patent No.: US 12,738,378 B2
(45) **Date of Patent: *Sep. 15, 2026**

(54) SYSTEMS AND METHODS FOR PERSONALIZED CARDIOVASCULAR ANALYSES

(71) Applicant: TC1 LLC, St. Paul, MN (US)

(72) Inventors: Eric Lee, Oakland, CA (US); Daniel I. Harjes, Carlisle, MA (US)

(73) Assignee: TC1 LLC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/383,185

(22) Filed: Oct. 24, 2023

(65) Prior Publication Data

US 2024/0055120 A1 Feb. 15, 2024

Related U.S. Application Data

(63) Continuation of application No. 17/118,951, filed on Dec. 11, 2020, now Pat. No. 11,837,364.

(Continued)

(51) Int. Cl.

*G16H 50/00* (2018.01)
*G16H 10/60* (2018.01)
*G16H 40/67* (2018.01)

(52) U.S. Cl.

CPC ............. *G16H 50/00* (2018.01); *G16H 10/60* (2018.01); *G16H 40/67* (2018.01)

(58) Field of Classification Search

CPC ......... G16H 50/00; G16H 40/67; G16H 10/60

(Continued)

(56) References Cited

U.S. PATENT DOCUMENTS 7,801,591 B1 9/2010 Shusterman
8,388,530 B2 3/2013 Shusterman (Continued)

FOREIGN PATENT DOCUMENTS

CN 103415320 A 11/2013
CN 105194799 A 12/2015

(Continued)

OTHER PUBLICATIONS

Wang, Y., Faragallah, G., Divo, E., & Simaan, M. A. (Jun. 2012). Feedback control of a rotary left ventricular assist device supporting a failing cardiovascular system. In 2012 American Control Conference (ACC) (pp. 1137-1142). IEEE. (Year: 2012).*

(Continued)

*Primary Examiner* — Winston R Furtado
(74) *Attorney, Agent, or Firm* — Armstrong Teasdale LLP

(57) ABSTRACT

Systems and methods for performing personalized cardiovascular analyses are provided. A method includes building, using a modeling and simulation computing device, a patient-specific model, storing, using the modeling and simulation computing device, the patient-specific model in a database, receiving, at the modeling and simulation computing device, remote monitoring data from at least one remote monitoring data source, and receiving, at the modeling and simulation computing device, clinical data from at least one clinical data source. The method further includes updating, using the modeling and simulation computing device, the patient-specific model using the remote monitoring data and the clinical data, performing, using the modeling and simulation computing device, at least one simulation on the updated patient-specific model, and outputting, from the modeling and simulation computing device, at least one output based on the at least one simulation.

20 Claims, 3 Drawing Sheets

Related U.S. Application Data

(60) Provisional application No. 62/951,312, filed on Dec. 20, 2019.

(58) Field of Classification Search
USPC .............................................................. 705/2
See application file for complete search history.

(56) References Cited

U.S. PATENT DOCUMENTS

| | | | | |
|---|---|---|---|---|
| 9,043,191 | B2 | 5/2015 | Grady | |
| 9,107,586 | B2 | 8/2015 | Tran | |
| 9,141,763 | B2 | 9/2015 | Sharma | |
| 2004/0039243 | A1 | 2/2004 | Bearnson | |
| 2004/0153128 | A1 | 8/2004 | Suresh | |
| 2012/0310297 | A1* | 12/2012 | Sweeney .................. | A61B 5/35 607/25 |
| 2013/0197881 | A1* | 8/2013 | Mansi .................... | G09B 23/30 703/2 |
| 2014/0187920 | A1 | 7/2014 | Millett | |
| 2017/0000422 | A1* | 1/2017 | Moturu ................ | A61B 5/0022 |
| 2017/0235915 | A1* | 8/2017 | Mansi .................... | G16H 50/30 705/3 |
| 2017/0340887 | A1* | 11/2017 | Engels ............... | A61N 1/36592 |
| 2019/0282743 | A1 | 9/2019 | Agarwal et al. | |
| 2019/0298903 | A1* | 10/2019 | Gillberg ............... | A61B 5/6805 |
| 2019/0336767 | A1 | 11/2019 | Klepfer | |

FOREIGN PATENT DOCUMENTS

| | | | | |
|---|---|---|---|---|
| WO | 2018108276 | A1 | 6/2018 | |
| WO | 2018134330 | A2 | 7/2018 | |
| WO | WO-2018126254 | A1 * | 7/2018 | ............. G09B 23/00 |
| WO | 2019195783 | A1 | 10/2019 | |

OTHER PUBLICATIONS

Kilic, A., Macickova, J., Duan, L., Movahedi, F., Seese, L., Zhang, Y., . . . & Padman, R. (2021). Machine learning approaches to analyzing adverse events following durable LVAD implantation. The Annals of Thoracic Surgery, 112(3), 770-777. (Year: 2021).*

International Search Report and Written Opinion for International Patent Application No. PCT/US2020/064450, mailed Apr. 1, 2021, 14 pages.

JP First Office Action, Application No. 2022-537239, dated Nov. 11, 2024, 8 pps.: with English Translation.

First Office Action for Chinese Patent Application No. 202080088673.0 dated May 7, 2026; 9 pp.

* cited by examiner

SYSTEMS AND METHODS FOR PERSONALIZED CARDIOVASCULAR ANALYSES

CROSS-REFERENCE TO RELATED APPLICATIONS

This application is a continuation of non-provisional application Ser. No. 17/118,951, filed Dec. 11, 2020 which claims priority to provisional application Ser. No. 62/951,312, filed Dec. 20, 2019, both of which are incorporated herein by reference in their entirety.

FIELD OF THE DISCLOSURE

This disclosure relates to monitoring patients with cardiovascular issues, and more particularly, this disclosure relates to executing patient-specific cardiovascular analyses.

BACKGROUND

Ventricular assist systems (VASs) may include ventricular assist devices (VADs), such as implantable blood pumps used for both short-term (i.e., days, months) and long-term (i.e., years or a lifetime) applications where a patient's heart is incapable of providing adequate circulation, commonly referred to as heart failure or congestive heart failure. A patient suffering from heart failure may use a VAS while awaiting a heart transplant or as a long-term destination therapy. In another example, a patient may use a VAS while recovering from heart surgery. Thus, a VAS can supplement a weak heart (i.e., partial support) or can effectively replace the natural heart's function. VASs can be implanted in the patient's body and powered by an electrical power source inside or outside the patient's body.

Understanding and managing the hemodynamic state of a heart failure patient may be relatively challenging. Further, additional complexity arises for VAD patients with one or more underlying conditions, such as right ventricle (RV) dysfunction, valve disorders, arrhythmias, etc.

One focus of next-generation VAD development is adding system enhancements to assist physicians in optimizing therapy to improve adverse event profiles and overall patient quality of life. Example enhancements include using improved sensing abilities (e.g., flow waveform sensing, pressure waveform sensing, accelerometers, etc.) in conjunction with closed loop control algorithms (e.g., pulsing and physiologic control). These enhancements may be utilized in so-called "Smart VADs".

However, with these new capabilities comes an increase in complexity and sophistication of patient management, particularly if a patient has additional devices, such as pacemakers or pulmonary artery (PA) pressure sensors. Thus, there is a need to educate and train physicians regarding how to manage complex patient/device system interactions, and to understand the meaning of new diagnostic tools as they come on line. Further, there is a need to simplify and consolidate cardiac assist device interfaces, to leverage remote monitoring to record patient/device data outside the clinic for extended periods, and to develop algorithms that can process and interpret device data to facilitate optimizing patient treatment. Accordingly, there is a need for a unified remote monitoring infrastructure.

BRIEF SUMMARY OF THE DISCLOSURE

In one embodiment, the present disclosure is directed to a method for performing personalized cardiovascular analyses. The method includes building, using a modeling and simulation computing device, a patient-specific model, storing, using the modeling and simulation computing device, the patient-specific model in a database, receiving, at the modeling and simulation computing device, remote monitoring data from at least one remote monitoring data source, and receiving, at the modeling and simulation computing device, clinical data from at least one clinical data source. The method further includes updating, using the modeling and simulation computing device, the patient-specific model using the remote monitoring data and the clinical data, performing, using the modeling and simulation computing device, at least one simulation on the updated patient-specific model, and outputting, from the modeling and simulation computing device, at least one output based on the at least one simulation.

In another embodiment, the present disclosure is directed to a computing device for performing personalized cardiovascular analyses. The computing device includes a memory device and a processor communicatively coupled to the memory device. The processor is configured to build a patient-specific model, store the patient-specific model in the memory device, receive remote monitoring data from at least one remote monitoring data source, receive clinical data from at least one clinical data source, update the patient-specific model using the remote monitoring data and the clinical data, perform at least one simulation on the updated patient-specific model, and output an output based on the at least one simulation.

In yet another embodiment, the present disclosure is directed to non-transitory computer-readable media having computer-executable instructions thereon. When executed by a processor of a computing device, the instructions cause the processor of the computing device to build a patient-specific model, store the patient-specific model in a database, receive remote monitoring data from at least one remote monitoring data source, receive clinical data from at least one clinical data source, update the patient-specific model using the remote monitoring data and the clinical data, perform at least one simulation on the updated patient-specific model, and output an output based on the at least one simulation.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The disclosure provides systems and methods for performing personalized cardiovascular analyses. A method includes building, using a modeling and simulation computing device, a patient-specific model, storing, using the modeling and simulation computing device, the patient-specific model in a database, receiving, at the modeling and simulation computing device, remote monitoring data from at least one remote monitoring data source, and receiving, at the modeling and simulation computing device, clinical data from at least one clinical data source. The method further includes updating, using the modeling and simulation computing device, the patient-specific model using the remote monitoring data and the clinical data, performing, using the modeling and simulation computing device, at least one simulation on the updated patient-specific model, and outputting, from the modeling and simulation computing device, at least one output based on the at least one simulation.

The embodiments described herein provide a cloud-based remote monitoring and simulation system that stores and maintains a patient-specific numerical cardiovascular model. The system uses machine learning and optimization techniques to continually update simulation parameters for the model using actual patient data collected from clinical data sources and remote monitoring data sources. The more data collected by the system, the more accurate the model. Because the model replicates a particular patient, the model may also be referred to as a "digital clone" of the particular patient.

Figure 1:
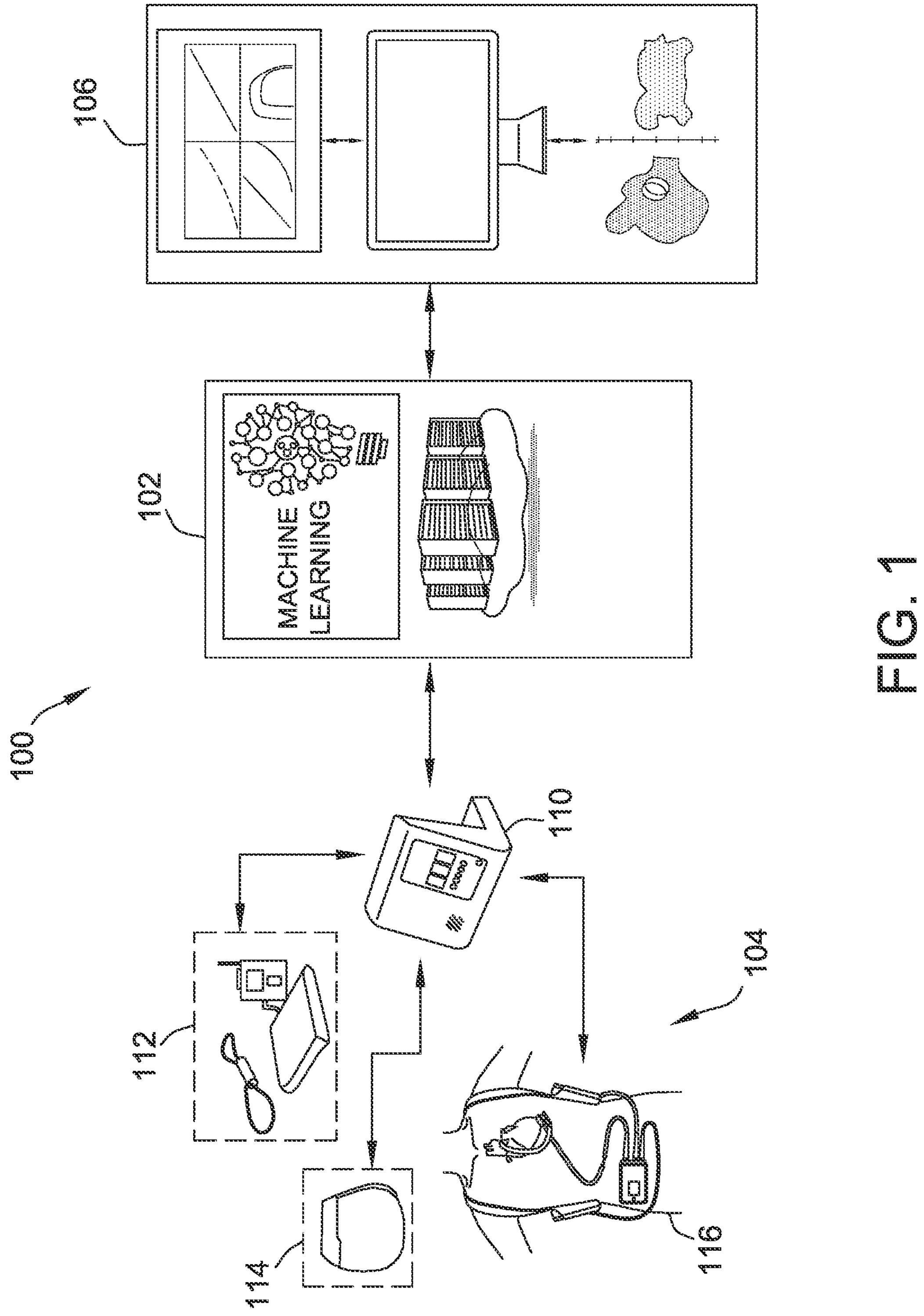
FIG. 1 is a schematic diagram of one embodiment of a remote monitoring and simulation system.

Referring now to the drawings wherein like reference numerals are used to identify identical components in the various views, FIG. 1 illustrates one embodiment of a remote monitoring and simulation system 100. System 100 includes a modeling and simulation computing device 102. In the exemplary embodiment, modeling and simulation computing device 102 is a cloud-based server system. Alternatively, modeling and simulation computing device 102 may be any computing device suitable for implementing the systems and methods described herein.

Modeling and simulation computing device 102 is communicatively coupled to a plurality of remote monitoring data sources 104 and a plurality of clinical data sources 106. To build and update a patient-specific model for a particular patient, modeling and simulation computing device 102 collects remote monitoring data associated with the patient from remote monitoring data sources 104 and clinical data associated with the patient from clinical data sources 106, as described herein. In some embodiments, the data may be time-stamped as it is received by modeling and simulation computing device 102.

Remote monitoring data sources 104 associated with the patient may include, for example, a patient monitoring device 110, a heart failure monitor 112, a cardiac resynchronization therapy (CRT) device 114, and a VAD 116. In some embodiments, patient monitoring device 110 initially collects remote data from other devices (e.g., heart failure monitor 112, CRT device 114, and VAD 116) and relays that remote monitoring data to modeling and simulation computing device 102. Alternatively, each device may independently transmit remote monitoring data to modeling and simulation computing device 102.

Remote monitoring data collected from remote monitoring data sources 104 may include patient hemodynamic data and device status data. For example, collected data may include pump flow waveforms, left ventricular (LV) pressure wave forms, and aortic pressure wave forms (e.g., from VAD 116). Also, collected remote monitoring data may additionally or alternatively include pulmonary artery (PA) pressure waveforms (e.g., from heart failure monitor 112), CRT data (e.g., from CRT device 114), and implantable cardiac monitor data. Those of skill in the art will appreciate that other types of remote monitoring data may also be collected.

Clinical data sources 106 may include, for example, a physician computing device, an electronic medical record system, etc. Further, clinical data for the patient may include, for example, in clinic measurements, such as right catheter measurements, echocardiogram data, blood pressure measurements, etc.

Figure 2:
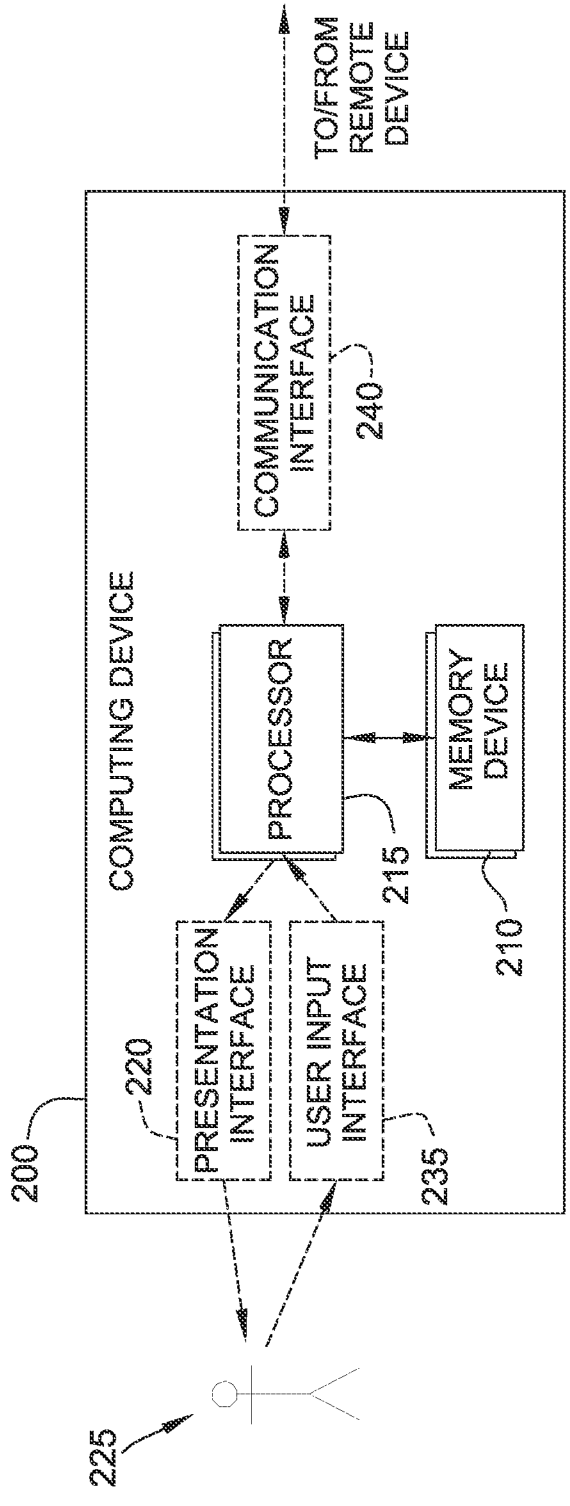
FIG. 2 is a block diagram of one embodiment of a computing device that may be used to implement the systems and methods described herein.

FIG. 2 illustrates one embodiment of a computing device 200 that may be used to implement the systems and methods described herein. Computing device 200 may be used, for example, to implement modeling and simulation computing device 102 (shown in FIG. 1). Computing device 200 includes at least one memory device 210 and a processor 215 that is coupled to memory device 210 for executing instructions. In some embodiments, executable instructions are stored in memory device 210. In this embodiment, computing device 200 performs one or more operations described herein by programming processor 215. For example, processor 215 may be programmed by encoding an operation as one or more executable instructions and by providing the executable instructions in memory device 210.

Processor 215 may include one or more processing units (e.g., in a multi-core configuration). Further, processor 215 may be implemented using one or more heterogeneous processor systems in which a main processor is present with secondary processors on a single chip. In another illustrative example, processor 215 may be a symmetric multi-processor system containing multiple processors of the same type. Further, processor 215 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In this embodiment, memory device 210 is one or more devices that enable information such as executable instructions and/or other data to be stored and retrieved. Memory device 210 may include one or more computer readable media, such as, without limitation, dynamic random access memory (DRAM), static random access memory (SRAM), a solid state disk, and/or a hard disk. Memory device 210 may be configured to store, without limitation, application source code, application object code, source code portions of interest, object code portions of interest, configuration data, execution events and/or any other type of data.

In this embodiment, computing device 200 includes a presentation interface 220 that is coupled to processor 215. Presentation interface 220 presents information to a user 225. For example, presentation interface 220 may include a display adapter (not shown) that may be coupled to a display device, such as a cathode ray tube, a liquid crystal display (LCD), an organic LED (OLED) display, and/or an "electronic ink" display. In some embodiments, presentation interface 220 includes one or more display devices. Input signals and/or filtered signals processed using the embodiments described herein may be displayed on presentation interface 220.

In this embodiment, computing device 200 includes a user input interface 235. User input interface 235 is coupled to processor 215 and receives input from user 225. User input interface 235 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 220 and user input interface 235.

Computing device 200, in this embodiment, includes a communication interface 240 coupled to processor 215. Communication interface 240 communicates with one or more remote devices. To communicate with remote devices, communication interface 240 may include, for example, a wired network adapter, a wireless network adapter, and/or a mobile telecommunications adapter.

Referring back to FIG. 1, using the remote monitoring data collected from remote monitoring data sources 104 and the clinical data connected from clinical data sources 106, modeling and simulation computing device 102 builds and updates a patient-specific model. The patient-specific model may be stored, for example, in memory device 210 (shown in FIG. 2).

Subsequently, modeling and simulation computing device 102 runs one or more simulations on the patient-specific model to facilitate optimizing patient treatment. Outputs of the simulations may be displayed, for example, on presentation interface 220 (shown in FIG. 2).

For example, prior to implanting a VAD in the patient, simulations may be run to simulate how the patient would respond to VAD therapy. In this scenario, the patient model may be built using data from heart failure monitor 112 and/or CRT device 114 and data from in-clinic measurements, as a VAD has not yet been implanted. These results of these simulations may aid the clinician in determining whether or not to implant a VAD, and determining which type of VAD to implant (e.g., LVAD, Bi-VAD, etc.).

After implantation of a VAD, simulations may be run on the patient specific-model to simulate operation of the VAD. For example, the impact of adjusting pump speed and/or adjusting pulse type may be simulated. In another example, the impact of adjusting medications and/or fluid volume may be simulated.

Further, in some embodiments, modeling and simulation computing device 102 analyzes the patient-specific model (e.g., using machine learning and/or other artificial intelligence techniques). The outputs of these analyses may be displayed, for example, on presentation interface 220 (shown in FIG. 2).

For example, as a result of analyzing the patient-specific model, modeling and simulation computing device 102 may recommend changes to VAD parameters (e.g., pump speed) and/or medication to achieve desirable hemodynamic results (e.g., a desired LV pressure profile). In another example, modeling and simulation computing device 102 may track changes in hemodynamic properties over time to identify patterns and/or generate alerts. Tracked hemodynamic properties may include LV/RV systolic function, pulmonary and systemic vascular resistance, vessel compliance, fluid/volume status, valve functionality, hematocrit values, etc. In one example, modeling and simulation computing device 102 tracks cardiac recovery (e.g., ventricle function capacity) and optimizes recovery protocols on a patient-specific basis (e.g., by recommending medication dose/timing, pump weaning, pulse types, etc.).

In addition, based on analysis of the patient-specific model, modeling and simulation computing device 102 may generate recommended device settings. For example, modeling and simulation computing device 102 may generate recommended settings for pump speed, physiologic control settings, pulse type, and/or pacemaker settings. In some embodiments, modeling and simulation computing device 102 may control one or more of remote monitoring data sources 104. For example, modeling and simulation computing device 102 may generate and transmit control signals to CRT device 114 and/or VAD 116 that instruct CRT device 114 and/or VAD 116 to adjust their settings.

In the embodiments, described herein, the patient-specific model is an online numerical model that continually updates to match the patient's current condition based on data received from remote monitoring data sources 104 and clinical data sources 106. The more data available to and incorporated into the model, the more accurate the simulations and analysis performed by modeling and simulation computing device 102.

The patient-specific model may be, for example, a high fidelity lumped parameter numerical model that simulates a human circulatory system. Further, the model may include features that allow the model to better match actual patients, such as physiologic feedback mechanisms and non-linear outflow graft dynamics.

For example, in one embodiment, the model includes approximately seventy-five parameters that define the behavior of the entire circulatory system. By varying these parameters, the model can replicate the behavior of most patients (excluding sever autoregulation disorders).

Given the variability of VAD patient properties and hemodynamics, in some embodiments, the model is tuned to match a specific patient. Specifically, machine learning and/or other artificial intelligence techniques are used to systematically vary key model parameters until the simulated model replicates actual hemodynamic and pump parameter data (e.g., ventricle dimensions, PA pressures, etc.) from clinical data.

In some embodiments, modeling and simulation computing device 102 also builds a database of generalized models. For example, each generalized model may be built using corresponding clinical study data. The generated database thus includes a plurality of anonymized models. These models may be searchable, for example, based on generic patient properties such as gender, race, weight, BMI, cardiac index, INTERMACS classification, etc. This searchable database allows a user to search for an anonymized model based on properties of a patient of interest, and use that anonymized model as a "starting point" for the patient specific model. Notably, the more similar to the anonymized model to the patient of interest, the faster the anonymized model will converge to an accurate patient-specific model. Further, in some embodiments, modeling and simulation computing device 102 receives existing clinical and/or demographic data associated with the patient, and automatically selects an anonymized model from the database based on the existing clinical and/or demographic data.

Using modeling and simulation computing device 102, a user (e.g., a clinician) is able to clearly visualize and understand the mechanisms behind various patient/device interactions. Further, by running simulations, the user can "virtually" experiment with changing pump speed, medication, fluid volume, etc., and observe the quantified expected hemodynamic response. Further, using modeling and simulation computing device 102, the user can simulate various events (e.g., dehydration, arrhythmia, exercise, acute hypertension, etc.) to observe the expected outcome and assist in future recognition of such events.

Modeling and simulation computing device 102 also continually updates key model parameters (e.g., ventricle elastance curves, valve resistance, aortic compliance, etc.) using machine learning and/or other artificial intelligence techniques to ensure that simulation results match or closely track clinical data. That is, the patient-specific model estimates various patient parameters without a direct physical measurement, which is highly useful for tracking physiological changes over time such as ventricle function, valve leakage, etc.

To demonstrate the efficacy of the systems and methods described herein, an example case study will now be described. Specifically, the following case study illustrates how the systems and methods described herein could be used to aid in the treatment of a dilated cardiomyopathy (DCM) heart failure patient through the continuum of heart failure. Those of skill will appreciate that similar techniques could be applied to other heart failure patients as well. This case study is purely fictional, and is intended to demonstrate how the systems and methods described herein could be implemented.

In this example, assume a patient gradually develops an underlying electrophysiological disorder (e.g., left bundle branch block) resulting in deteriorating LV functionality. The patient is initially asymptomatic and unaware of any problems. However, over time, electrical conduction issues worsen, ventricular pumping function becomes compromised, and the patient occasionally shows minor heart failure (HF) symptoms (i.e., stage II).

Despite activation of the renin-angiotensin (RAS) feedback system, the patient is unable to maintain sufficient cardiac output and arterial pressure. Chronically high ventricular pressures cause the LV to become further dilated, further compromising pumping function. The patient is now symptomatic to the point where they see a cardiologist (i.e., stage III). The cardiologist performs a full hemodynamic workup, measures an ejection fraction of 30%, and identifies the underlying left bundle branch block disorder.

At this point, the patient is implanted with a pacemaker and a heart failure monitor (e.g., a PA pressure sensor), and assigned a typical HF medication regiment. The patient is then registered with an account for a remote monitoring system (which may be the same as or separate from modeling and simulation computing device 102) and given required equipment to enable remote monitoring of the devices. Further, in accordance with the systems and methods described herein, the clinician uses modeling and simulation computing device 102 to initialize a patient-specific model for the patient. For example, modeling and simulation computing device 102 may automatically select initial parameters for the model based on existing clinical and/or demographic data for the patient.

The pacemaker initially improves cardiac pumping capacity and alleviates HF systems visible to the patient, returning to stage II. However, prior chronic LV dilation has caused the heart to become mechanically compromised and high ventricular filling pressures persist. Over the following months/years, the LV continues to dilate despite successful pacing. The heart failure monitor tracks PA pressures drifting higher, and these results are passed to the remote monitoring system and are visible to the clinician. Further, the patient-specific model has been updating based on data received from the pacemaker and heart failure monitor, and now has a matching confidence level to the actual patient of 65%. Modeling and simulation computing device 102 is also reporting, based on analysis of the model, reduced LV systolic function.

The clinician decides to have the patient return to the clinic to receive a full hemodynamic workup despite generally feeling okay. Results indicate a severely dilated LV and poor general hemodynamics. These in-clinic results are provided to modeling and simulation computing device 102, and the matching confidence level increases to 75%. The clinician adjusts medication and sends the patient home for remote observation.

Over the next few months, HF symptoms worsen to stage IV, and the patient is unable to perform daily tasks. The patient-specific model suggests very low, and steadily worsening, LV systolic function. Eventually the patient returns to the clinic for another hemodynamic workup. Results are poor, with an ejection fraction of 20% and low cardiac index. The patient appears to be a good recovery candidate (younger with only a couple of years in HF), but a poor transplant candidate (blood type O, weighing over 100 kilograms).

Using modeling and simulation computing device 102, the clinician simulates how the patient would respond to VAD therapy (the matching confidence level is now 80%). The patient-specific model indicates a favorable hemodynamic response to VAD support and strong RV function. Accordingly, the decision is made to implant a VAD capable of communicating data to modeling and simulation computing device 102.

Within weeks after the VAD implantation, the patient is healthy and walking around with no HF symptoms (i.e., stage I). The patient-specific model, which is now also incorporating an abundance of data from the VAD, has now reached a matching confidence level of 95%. After three months, analysis of the patient-specific model by the modeling and simulation computing device 102 is now indicating improved LV systolic function and remodeling. The clinician reviews the logged data and allows the modeling and simulation computing device 102 to instruct the VAD to initiate a recovery protocol, in which the VAD periodically reduces pump speed to automatically "train" the LV.

After another two months, analysis of the patient-specific model by the modeling and simulation computing device 102 indicates consistently strong LV function, and the weaning algorithms have been implemented to reduce VAD pump speed to relatively low levels such that VAD support is minimal. Using modeling and simulation computing device 102, the clinician simulates removal of the VAD, and the results of the simulation indicate a high probability of recovery. Thus, the decision is made to explant the VAD. Two years after explanting the VAD, the patient shows stable durable recovery. The patient-specific model maintained by modeling and simulation computing device 102 is still active using available data from the pacemaker and heart failure monitor.

Accordingly, this case study demonstrates the advantages realized using the systems and methods described herein.

Figure 3:
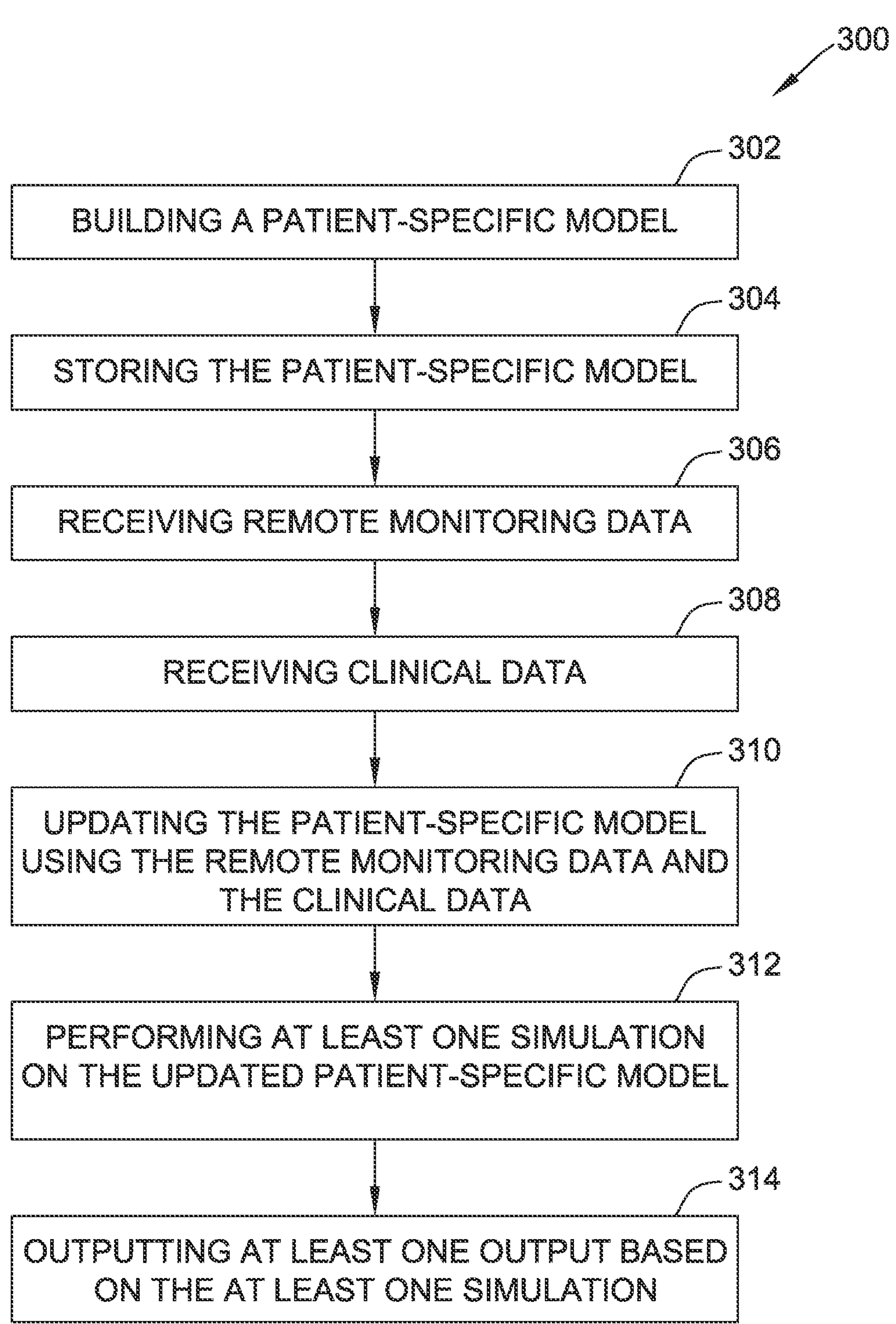
FIG. 3 is a block diagram of a method of performing personalized cardiovascular analyses.

FIG. 3 is a block diagram of a method 300 of performing personalized cardiovascular analyses. Method 300 may be implemented, for example, by modeling and simulation computing device 102 (shown in FIG. 1).

Method 300 includes building 302 a patient-specific model. Method 300 further includes storing 304 the patient-specific model in a database. In addition, method 300 includes receiving 306 remote monitoring data from at least one remote monitoring data source, and receiving 308 clinical data from at least one clinical data source. Method 300 further includes updating 310 the patient-specific model using the remote monitoring data and the clinical data. Further, method 300 includes performing 312 at least one simulation on the updated patient-specific model and outputting 314 at least one output based on the at least one simulation.

The systems and methods described herein include building, using a modeling and simulation computing device, a patient-specific model, storing, using the modeling and simulation computing device, the patient-specific model in a database, receiving, at the modeling and simulation computing device, remote monitoring data from at least one remote monitoring data source, and receiving, at the modeling and simulation computing device, clinical data from at least one clinical data source. The systems and methods further include updating, using the modeling and simulation computing device, the patient-specific model using the remote monitoring data and the clinical data, performing, using the modeling and simulation computing device, at least one simulation on the updated patient-specific model, and outputting, from the modeling and simulation computing device, at least one output based on the at least one simulation.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A computer-implemented method for performing personalized cardiovascular analyses, the method comprising:

receiving, at a modeling and simulation computing device, remote monitoring data from at least one remote monitoring data source, the at least one remote monitoring data source including a ventricular assist device (VAD) implanted in a particular patient, the remote monitoring data including at least actual hemodynamic data related to function of an impaired circulatory system of the particular patient under assistance from the VAD;

updating, using the modeling and simulation computing device, a patient-specific model using the remote monitoring data received from the VAD, the patient-specific model representing the impaired circulatory system of the particular patient, wherein updating the patient-specific model comprises varying parameters of the patient-specific model until the patient-specific model replicates the actual hemodynamic data for the particular patient;

performing, using the modeling and simulation computing device, at least one simulation using the updated patient-specific model to simulate operation of the impaired circulatory system of the particular patient under assistance from the VAD in response to hemodynamic events related to further impairment, treatment, or recovery of the impaired circulatory system;

analyzing, using the modeling and simulation computing device, the updated patient-specific model to generate an adjusted operating parameter for the VAD based on a respective at least one outcome of the at least one simulation; and controlling operation of the VAD by transmitting a control signal including the adjusted operating parameter to the VAD, the control signal causing the VAD to adjust operation and begin operating at the adjusted operating parameter.

2. The method of claim 1, further comprising displaying a recommendation including the adjusted operating parameter.

3. The method of claim 1, further comprising continuing said receiving remote monitoring data from the VAD and updating the patient-specific model based on the remote monitoring data, using the modeling and simulation computing device, during and after operation of the VAD at the adjust operating parameter.

4. The method of claim 1, further comprising:

generating a database including a plurality of anonymized patient models; and initializing the patient-specific model by selecting one of the plurality of anonymized patient models as the patient-specific model based on clinical or demographic data of the particular patient.

5. The method of claim 1, further comprising:

receiving, at the modeling and simulation computing device, clinical data from at least one clinical data source; and updating the patient specific model using the clinical data.

6. The method of claim 1, wherein analyzing the updated patient-specific model comprises analyzing the updated patient-specific model using machine learning.

7. A computing device for performing personalized cardiovascular analyses, the computing device comprising:

a memory device; and a processor communicatively coupled to the memory device, the processor configured to:

receive remote monitoring data from at least one remote monitoring data source, the remote monitoring data including at least actual hemodynamic data for a particular patient, the at least one remote monitoring data source including at least one of a ventricular assist device (VAD) and a cardiac resynchronization therapy (CRT) device implanted in the particular patient;

update a patient-specific model using the remote monitoring data, the patient specific model representing a circulatory system of the particular patient, wherein to update the patient-specific model, the processor is configured to vary parameters of the patient-specific model until the patient-specific model replicates the actual hemodynamic data for the particular patient;

perform at least one simulation on the updated patient-specific model to simulate operation of the circulatory system of the particular patient during an event to i) predict an expected outcome of the event in the particular patient and ii) assist in recognizing a future occurrence of the event in the particular patient, the event including a dehydration event, an arrhythmia event, an exercise event, or an acute hypertension event, wherein the at least one simulation includes simulating removal of the VAD from the particular patient;

analyze the updated patient-specific model to generate an adjusted operating parameter; and control operation of the VAD by transmitting a control signal including the adjusted operating parameter to the VAD, the control signal and adjusted operating parameter causing the VAD to periodically reduce pump speed.

8. The computing device of claim 7, wherein the processor is further configured to output a recommendation including the adjusted operating parameter.

9. The computing device of claim 7, wherein the processor is further configured to build the patient-specific model.

10. The computing device of claim 9, wherein to build the patient-specific model, the processor is configured to generate a database including a plurality of anonymized patient models; and select one of the plurality of anonymized patient models as the patient-specific model.

11. The computing device of claim 7, wherein the processor is further configured to:

receive clinical data from at least one clinical data source; and update the patient specific model using the clinical data.

12. The computing device of claim 7, wherein the processor is further configured to analyze the updated patient-specific model using machine learning.

13. Non-transitory computer-readable media having computer-executable instructions thereon, wherein when executed by a processor of a computing device, cause the processor of the computing device to:

receive remote monitoring data from at least one remote monitoring data source, the at least one remote monitoring data source including a ventricular assist device (VAD) implanted in a particular patient, the remote monitoring data including at least actual hemodynamic data related to function of an impaired circulatory system of the particular patient under assistance from the VAD;

update a patient-specific model using the remote monitoring data received from the VAD, the patient-specific model representing the impaired circulatory system of the particular patient, wherein to update the patient-specific model, the instructions cause the process to vary parameters of the patient-specific model until the patient-specific model replicates the actual hemodynamic data for the particular patient;

perform at least one simulation using the updated patient-specific model to simulate operation of the circulatory system of the particular patient under assistance from the VAD in response to hemodynamic events related to further impairment, treatment, or recovery of the impaired circulatory system;

analyze the updated patient-specific model to generate an adjusted operating parameter for the VAD based on a respective at least one outcome of the at least one simulation; and control operation of the VAD by transmitting a control signal including the adjusted operating parameter to the VAD, the control signal causing the VAD to adjust operation and begin operating at the adjusted operating parameter.

14. The non-transitory computer-readable media of claim 13, wherein the instructions further cause the processor to output a recommendation including the adjusted operating parameter.

15. The non-transitory computer-readable media of claim 13, wherein the instructions further cause the processor to continuing receiving remote monitoring data from the VAD and updating the patient-specific model based on the remote monitoring data, during and after operation of the VAD at the adjust operating parameter.

16. The non-transitory computer-readable media of claim 13, wherein the instructions further cause the processor to:

generate a database including a plurality of anonymized patient models; and initialize the patient-specific model by selecting one of the plurality of anonymized patient models as the patient-specific model based on clinical or demographic data of the particular patient.

17. The non-transitory computer-readable media of claim 13, wherein the instructions further cause the processor to:

receive clinical data from at least one clinical data source; and update the patient specific model using the clinical data.

18. The non-transitory computer-readable media of claim 13, wherein the instructions further cause the processor to analyze the updated patient-specific model using machine learning.

19. The non-transitory computer-readable media of claim 13, wherein the parameters of the patient-specific model are selected from the group consisting of ventricle elastance curves, valve resistance, aortic compliance, ventricle dimensions, and pulmonary artery pressure.

20. The computer-implemented method for performing personalized cardiovascular analyses of claim 1, wherein updating the patient-specific model comprises varying parameters of the patient-specific model selected from the group consisting of ventricle elastance curves, valve resistance, aortic compliance, ventricle dimensions, and pulmonary artery pressure.

* * * * *